| United States Patent [19] | [11] Patent Number: 4,714,493 |
| Kogan et al. | [45] Date of Patent: Dec. 22, 1987 |

[54] ISOTHIOUREA HERBICIDAL COMPOSITION

[75] Inventors: Marcelo Kogan, Wilton, Conn.; Stephen E. Dinizo, San Lorenzo; Llewellyn W. Fancher, New Castle, both of Calif.

[73] Assignee: Stauffer Chemical Company, Westport, Conn.

[21] Appl. No.: 737,639

[22] Filed: May 24, 1985

[51] Int. Cl.$^4$ ............... A01N 38/08; C07C 119/18
[52] U.S. Cl. ....................................... 71/99; 558/5
[58] Field of Search .................... 260/453.4; 71/99; 558/5

[56] References Cited

U.S. PATENT DOCUMENTS

| 2,559,585 | 7/1951 | Beck et al. | 260/453.4 |
| 2,780,535 | 2/1957 | Snyder | 260/453.4 |
| 3,879,190 | 4/1975 | Fuchs | 558/5 |
| 3,896,160 | 7/1975 | Gaetzi | 558/5 |
| 4,017,529 | 4/1977 | Fuchs | 558/5 |

*Primary Examiner*—Henry R. Jiles
*Assistant Examiner*—Robert C. Whittenbaugh

[57] ABSTRACT

This invention relates to the herbicide N,N'-(N"-isopropylcarbamyl,N'''-isopropylcarbamyl)-S-ethylisothiourea, its use and process for making the same.

3 Claims, No Drawings

ISOTHIOUREA HERBICIDAL COMPOSITION

This invention relates to a herbicide compound. More specifically, this invention relates to a single compound that is selective to sugarcane and plantation crops such as coffee, citrus fruits, mangoes and the like.

DESCRIPTION OF THE INVENTION

It has been found that the compound identified as N,N'-(N''-isopropylcarbamyl,N'''-isopropylcarbamyl)-S-ethylisothiourea has very selective herbicidal activity in regard to sugarcane and plantation crops. This compound is not tolerant to crops such as corn, cotton, soybeans, sunflower and rice.

The process of manufacturing this compound is basically a twostep operation as follows:

(a) One mole of thiourea is reacted with 1.0 to 1.6, preferably 1.1 moles of ethyl bromide, ethyl iodide or ethyl chloride in the presence of a polar solvent such as water or ethyl alcohol. This reaction is carried out at reflux temperature or under pressure at elevated temperature to form S-ethylisothiouronium halide intermediate compound.

(b) The S-ethylisothiouronium halide salt formed in step (a) is reacted with isopropyl isocyanate in the presence of triethylamine, alkali metal carbonate such as sodium or potassium carbonate or sodium or potassium bicarbonate in the presence of a polar solvent such as dioxane, dimethylsulfoxide, dimethylformamide, ethyl acetate or water with a non-polar co-solvent such as toluene. This reaction is carried out at temperatures ranging between ambient and about 100° C. to form the product N,N'-(N''-isopropylcarbamyl,N'''-isopropylcarbamyl)-S-ethylisothiourea. When the reaction of this step is completed, the solution is washed with dilute hydrochloric acid and/or water and the organic phase is stripped to give the product. If triethylamine is used, the aqueous layer is made basic with 50% caustic and the triethylamine is separated, distilled and recycled. The aqueous layer is neutralized and discarded and the distillation residues are also discarded.

The reaction, as noted in steps (a) and (b) above, provide a yield of about 70–90% of the end product. The isopropyl isocyanate used in step (b) as defined above is normally purchased from the open commercial market, but can be manufactured by reacting isopropylamine with phosgene in the presence of an inert solvent to provide isopropyl isocyanate.

The compound of this invention is active as a pre-emergent surface herbicide and as a post-emergent surface applied herbicide. In order to illustrate the merits of this herbicide, the following Table is provided on the test procedures.

The active ingredient of the application was formulated into an acceptable form for spraying. Thus, a solution was made containing 240 milligrams (mg) of herbicide in a 1:1 mixture of 20 milliliters (ml) acetone and 20 ml of water. To this mixture was added 1% by volume Tween ® 20 (polyoxyethylene sorbitan monolaruate). In all of the tests, the cultivated plants were reared from seed in trays containing a sandy, fumigated soil. For the pre-emergent surface (PES) tests, the trays were seeded the day prior to application. For the post-emergent (POES) tests, the trays were seeded 12 days prior to application. At the proper time, the trays were sprayed with the active ingredient at various levels of application for treatment. The treated plants were kept at optimum light, water and temperature during the test procedures. The results of this test are as follows.

TABLE I

| Rate kg/ha | Grasses | | | | | | | Broadleaves | | | | | | | | | Perennials | |
|---|---|---|---|---|---|---|---|---|---|---|---|---|---|---|---|---|---|---|
| | BRP | CEE | DIH | ECG | ELI | SEG | X | ACH | BIP | BRC | CAO | CON | EMS | IPA | SIR | X | SOH | CYR |
| % WEED CONTROL - PRE-EMERGENT APPLICATION | | | | | | | | | | | | | | | | | | |
| 0.25 | 0 | 0 | 0 | 0 | 0 | 0 | 0 | 0 | 0 | 98 | 98 | 75 | 20 | 95 | 0 | 48 | 0 | 0 |
| 0.50 | 95 | 50 | 60 | 98 | 75 | 70 | 75 | 50 | 95 | 100 | 100 | 80 | 90 | 100 | 60 | 84 | 0 | 0 |
| 1.00 | 98 | 98 | 90 | 100 | 90 | 90 | 94 | 60 | 98 | 100 | 100 | 100 | 99 | 100 | 80 | 92 | 0 | 0 |
| 2.00 | 99 | 98 | 100 | 100 | 95 | 96 | 98 | 90 | 98 | 100 | 100 | 100 | 100 | 100 | 90 | 97 | 0 | 0 |
| 4.00 | 100 | 100 | 100 | — | 100 | 100 | 100 | 100 | 100 | — | 100 | — | 100 | 100 | 90 | 99 | — | — |
| % WEED CONTROL - POST-EMERGENCE APPLICATION | | | | | | | | | | | | | | | | | | |
| 0.25 | 50 | 0 | 51 | 90 | 05 | 15 | 28 | 80 | 0 | 100 | 90 | 90 | 0 | — | 95 | 65 | 0 | 0 |
| 0.50 | 100 | 95 | 20 | 100 | 15 | 25 | 59 | 100 | 80 | 100 | 95 | 95 | 100 | — | 100 | 96 | 0 | 30 |
| 1.00 | 100 | 98 | 30 | 100 | 30 | 50 | 68 | 100 | 90 | 100 | 95 | 100 | 100 | — | 100 | 98 | 50 | 50 |
| 2.00 | 100 | 100 | 40 | 100 | 25 | 80 | 74 | 100 | 95 | 100 | 100 | 100 | 100 | — | 100 | 99 | 80 | 80 |

X = Average
— = not tested
kg/ha — kilograms/hectare
BRP = *Brachiaria plantaginea*
CEE = *Cenchrus echinatus*
DIH = *Digitaria horizontalis*
ECG = *Echinochloa crusgalli*
ELI = *Eleusine indica*
SEG = *Setaria geniculata*
ACH = *Acanthospermum hispidum*
BIP = *Bidens pilosa*
BRC = *Brassica campestris*
CAO = *Cassia occidentalis*
CON = *Commelina nudiflora*
EMS = *Emilia sonchifolia*
IPA = *Ipomoea acuminata*
SIR = *Sida rhombifolia*
SOH = *Sorghum halepense*
CYR = *Cyperus rotundus*

TABLE II

CROP SELECTIVITY: PRE-EMERGENT AND POST-EMERGENT APPLICATIONS

| Rate kg/ha | Corn | Cotton | Soybeans | Sunflower | Rice | Sugarcane |
|---|---|---|---|---|---|---|
| % Control - Pre-Emergent | | | | | | |
| 0.25 | 0 | 0 | 40 | 30 | 50 | 0 |
| 0.50 | 10 | 10 | 70 | 100 | 95 | 0 |
| 1.00 | 70 | 60 | 80 | 100 | 100 | 0 |
| 2.00 | 100 | 100 | 90 | 100 | 100 | 0 |

TABLE II-continued

CROP SELECTIVITY: PRE-EMERGENT AND POST-EMERGENT APPLICATIONS

| Rate kg/ha | Corn | Cotton | Soybeans | Sunflower | Rice | Sugarcane |
|---|---|---|---|---|---|---|
| | | | % Control - Post-Emergent | | | |
| 0.25 | 5 | 35 | 60 | 100 | 95 | 0 |
| 0.50 | 40 | 80 | 90 | 100 | 100 | 0 |
| 1.00 | 95 | 90 | 95 | 100 | 100 | 45* |
| 2.00 | 100 | 100 | 95 | 100 | 100 | 50* | kg/ha = kilogram/hectare
*Stunted, but recovered.

As can be seen from the above tables, the compound of this invention is very active as a broadleaf and grass control compound and is very selective in its crop tolerances. Specifically, sugarcane is the only one that is tolerant at all rates.

The same pre-emergent and post-emergent surface application of the active compound of this invention was also applied to citrus and coffee crops with the same results. All the weeds as defined above in Table I were controlled and there was no residual phytoxicity in regard to the crop plants.

The active compound of this invention can be used in any form, but is most preferably formulated with inert adjuvant carriers such as emulsifiable concentrate, a powder, liquid, wettable powder, granules, and like formulations. The amount of active ingredient used for application can range between about 0.25 kg/ha to about 10 kg/ha.

What is claimed is:

1. The compound N,N'-(N''-isopropylcarbamyl,N'''-isopropylcarbamyl)-S-ethylisothiourea.

2. The process of controlling weed species in crop plants selected from surgarcane and plantation crops comprising applying to the habitat where control is desired an herbicidally effective amount of the compound of claim 1.

3. A herbicidal composition comprising a herbicidally effective amount of the compound of claim 1 with a herbicidally suitable inert adjuvant carrier.

* * * * *